(12) United States Patent
Horn

(10) Patent No.: US 8,449,588 B2
(45) Date of Patent: May 28, 2013

(54) DURATION AND COMFORT IN COOLING VEST

(75) Inventor: Stephen Taylor Horn, White Stone, VA (US)

(73) Assignee: Stephen T. Horn and Phyllis Horn Joint Tenure IP Common, White Stone, VA (US)

( * ) Notice: Subject to any disclaimer, the term of this patent is extended or adjusted under 35 U.S.C. 154(b) by 1626 days.

(21) Appl. No.: 11/526,325

(22) Filed: Sep. 25, 2006

(65) Prior Publication Data

US 2008/0077210 A1 Mar. 27, 2008

(51) Int. Cl.
*A61F 7/00* (2006.01)
*A61F 7/10* (2006.01)

(52) U.S. Cl.
USPC ............... 607/108; 607/104; 607/112; 2/102

(58) Field of Classification Search
USPC .......................................... 607/104, 108, 114
See application file for complete search history.

(56) References Cited

U.S. PATENT DOCUMENTS

| | | | |
|---|---|---|---|
| 3,507,321 A | 4/1970 | Palma | |
| 3,570,264 A | 3/1971 | Curtis | |
| 3,610,323 A | 10/1971 | Troyer | |
| 3,950,789 A * | 4/1976 | Konz et al. | 2/93 |
| 4,033,354 A * | 7/1977 | De Rosa | 607/108 |
| 4,170,793 A | 10/1979 | O'Brien | |
| 4,405,348 A * | 9/1983 | Pasternack | 62/259.3 |
| 4,856,294 A * | 8/1989 | Scaringe et al. | 62/259.3 |
| 4,964,282 A | 10/1990 | Wagner | |
| 4,998,415 A | 3/1991 | Larsen | |
| 5,072,455 A | 12/1991 | St. Ours | |
| 5,146,625 A * | 9/1992 | Steele et al. | 2/102 |
| 5,289,695 A * | 3/1994 | Parrish et al. | 62/259.3 |
| 5,302,806 A * | 4/1994 | Simmons et al. | 219/211 |
| 5,305,471 A * | 4/1994 | Steele et al. | 2/102 |
| 5,415,222 A | 5/1995 | Colvin | |
| 5,484,448 A * | 1/1996 | Steele et al. | 607/108 |
| 5,722,482 A * | 3/1998 | Buckley | 165/10 |
| 6,125,645 A | 10/2000 | Horn | |
| 6,189,149 B1 * | 2/2001 | Allen | 2/102 |
| 6,915,641 B2 | 7/2005 | Harvie | |
| 2006/0201178 A1 * | 9/2006 | Smolko et al. | 62/259.3 |
| 2006/0201187 A1 * | 9/2006 | Smolko et al. | 62/315 |
| 2006/0276089 A1 * | 12/2006 | Amarasinghe et al. | 442/121 |

\* cited by examiner

*Primary Examiner* — Linda Dvorak
*Assistant Examiner* — Kaitlyn Smith

(57) ABSTRACT

The present invention is a cooling vest which has a type of phase change heat sink that particularly lends itself to layering of the heat sinks on the body. The heat sinks are quilted and have a means for the transportation of moisture through them and the means of transportation of air through channels in the quilted heat sinks. Thus they can remove moisture from the surface of the body and remain flexible.

20 Claims, 3 Drawing Sheets

Figure 8:
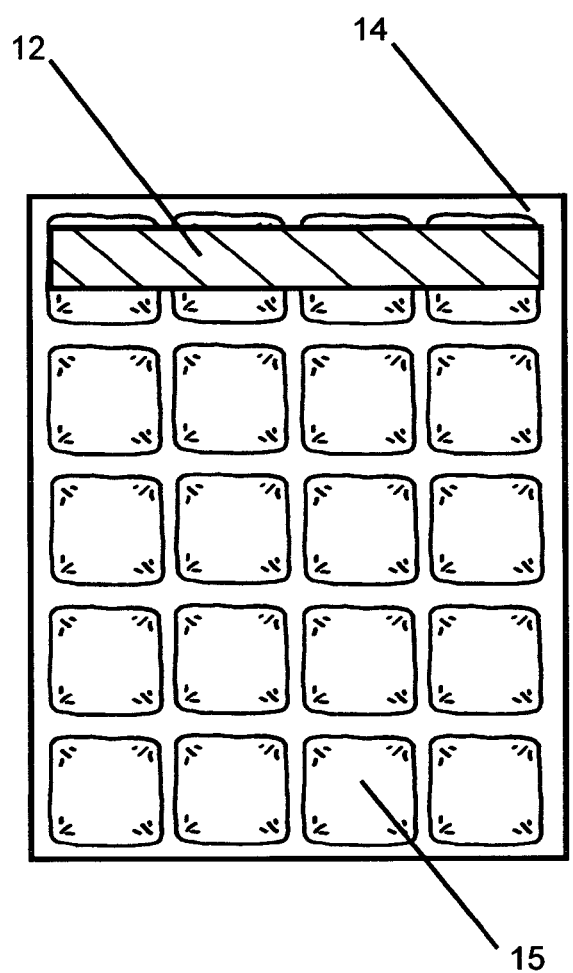

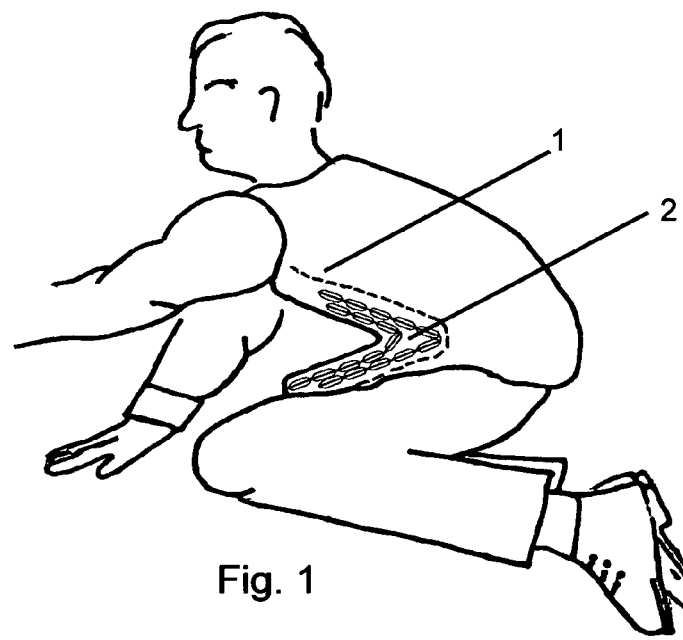
Fig. 1
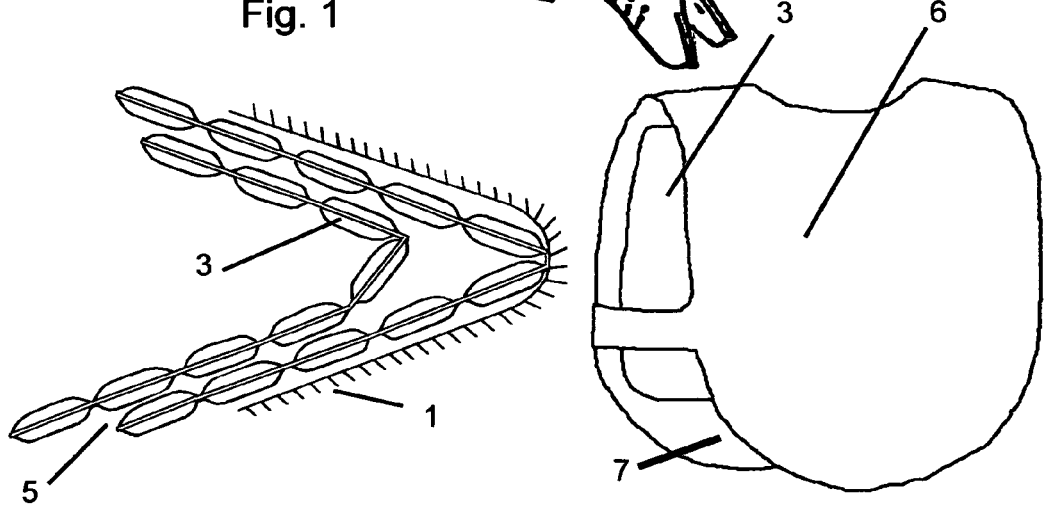
Fig. 2
Fig. 3

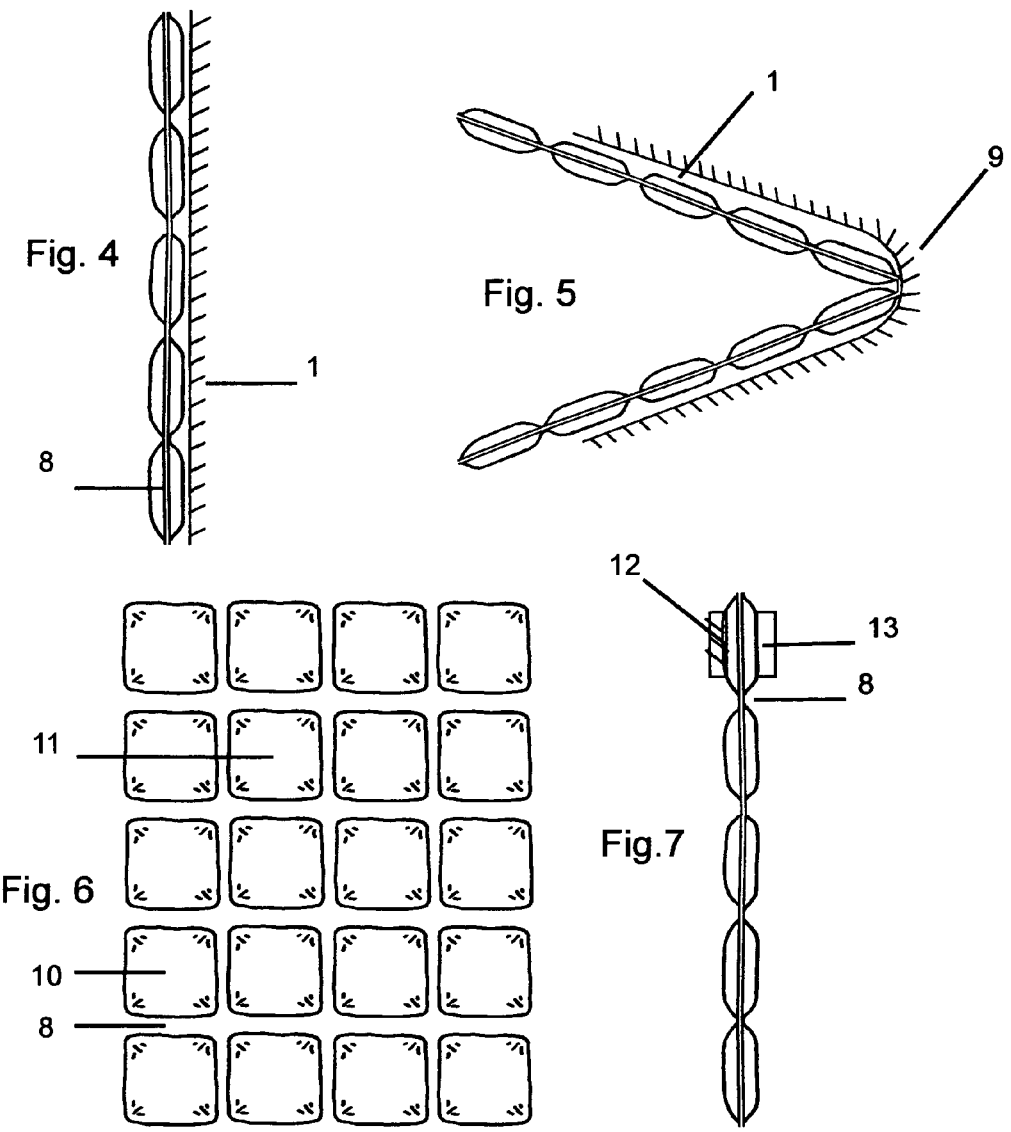

DURATION AND COMFORT IN COOLING VEST

CROSS-REFERENCE TO RELATED APPLICATIONS

None

FEDERALLY SPONSORED RESEARCH

None

SEQUENCE LISTING

None

1. FIELD OF THE INVENTION

The present invention is concerned with cooling vests specifically to cool the bodies of humans or animals.

2. DESCRIPTION OF THE PRIOR ART

Body garments for the purpose of cooling appear in the patent record taking many shapes and forms. However, most of these patents regard body garments that cool through a closed circulation system of a cool liquid through a piping network incorporated into a garment or through the specially constructed garment itself having its own circulatory network. Another focus of the prior art concerns cooling apparatus that cool through evaporative means. These devices are open systems, as opposed to the closed circulation systems mentioned above, that release cool air or vapor onto and over an individuals body to cool through evaporative means. Another patent uses the phase shift of a material in a vest to cool a person but makes no reference to the necessity of layering the phase shift material or the use of the layered phase shift material to induce air flow and remove moisture as a method of cooling by increasing the evaporation of moisture from the wearer or a means of keeping a person comfortable. The present invention works in a different fashion than these above mentioned patented inventions. It keeps the body comfortable by providing flexibility. Experiments done by the inventor show that the flexibility around the torso area in monolithic vests severely constricts lateral and bending movements necessary in a cramped work environment such as found in hot attics. The vest cools it is believed by absorbing heat directly from the body and by removing moisture away from the immediate environment around the body and condensing it on a cold surface. Thus reducing the relative humidity next to the body and increasing the evaporative cooling of the body and finally shielding the body from environmental heat. Experiments done by the inventor show that the transfer of body heat to a heat sink is more efficient and comfortable if the heat sink is used to reduce the humidity of immediate environment around the body and encourage the phase shift cooling that occurs when perspiration evaporates; rather than trying to absorb heat directly by placing the cold surface directly next to the body. This is believed to be because blood flow varies relative to the surface of the body and heat is tolerated better by some parts of the body than other parts. The body compensates it is believed by sweating more in some places than others (arm pits) and effects pilo-erections of surface hair as well as contracts capillaries near the skin to keep other places warmer. Typically when a cooling vest that uses a cold surface placed next to the skin is used several things are believed to occur. First evaporation of moisture is prevented due to a high humidity immediately established above the skin. A non-layered construction significantly prevents the movement of the wearer and hence limits the exchange of air under the vest. Second if the cold surface is to be effective it must be colder than usual for the skin as usually vests cover only a small portion of the body. This it is believed causes constriction of small capillaries below the surface of the skin and the contraction of muscles raising small hairs on the skin (goose bumps). Thus one system on the body fights the method of direct cooling the body by an application of a cold surface as found in circulated water systems or systems with cold packs of frozen chemicals. Finally different parts of the body maintain different temperatures and the body so regulates. No cold surface system can practically compensate for this as different activities require different temperatures. The human body is designed to be surrounded by different temperature air and can compensate for this if the humidity of this air is low enough. And in hot environments if the temperature of the immediate air can be reduced. The application of a large inflexible cold surface directly to the body is inefficient and uncomfortable.

The present invention uses a cold surface to condense moisture out of the immediate environment next to the body. The cold surface is provided by the frozen quilted and layered outer part of the garment. Channels are then provided between the quilt packages between the inner fabric layer of the vest and between the quilted heat sink layers of the vest, to remove the condensed moisture from the vest. The person is cool and dry. For argumentative purposes the prior art is presented as follows.

U.S. Pat. No. 3,507,321, issued to James R. Palma on Apr. 21, 1970, discloses clothing for cooling and heating the body. Palma's clothing affects the human body from the neck down by strategically locating heating coils and cooling conduits through the clothing. Temperature sensors are also incorporated into the clothing for accurate, electrical temperature control of the clothing. Moisture control is not considered.

U.S. Pat. No. 3,570,264, issued to Daniel L. Curtis on Mar. 16, 1971, discloses an evaporant cooling system comprising a light weight garment having a plurality of tubes connected in a parallel arrangement within the garment for the purposes of cooling the individual wearing same. This invention includes an inlet and an outlet manifold for circulating a liquid water-ammonia solution from a storage tank through the tubes. An exhaust port is also seen in fluid communication with the tubing for allowing the expended evaporant, the ammonia, to leave the system and further cool the individual. This is a cold surface system which cannot compensate for the bodies needs.

U.S. Pat. No. 3,610,323, issued to Dan E. Troyer on Oct. 5, 1971, also discloses an evaporative cooling garment to be worn by an individual. This garment is seen as a vest-like coat having a plurality of passageways incorporated therein to create a coat from these side-by-side passageways. These passageways are also seen as having a plurality of openings thereon. When used, the Troyer coat is supplied from a reservoir with a quantity of liquid coolant comprising a water and refrigerant, preferably Freon, through an inlet valve. As the body is cooled the refrigerant evaporates, leaves the system, and is replaced from the reservoir until the [such] refrigerant has been depleted. No consideration is made for the condensing of moisture from the body is made.

U.S. Pat. No. 3,744,053, issued to Eugene K. Parker on Jul. 10, 1973, discloses liquid loop garments for heating and cooling the body of and individual. This system is a closed system, releasing no liquid or gas for either heating or cooling purposes. Parker's garments are constructed of two, liquid U.S. Pat. No. 4,998,415, issued to John D. Larsen on Mar. 12, 1991, discloses a body cooling apparatus including a tubing system for circulating a fluid that is moved not only through the tubing within the apparatus but through a compressor and a condenser in order to remove heat away from the body of an individual wearing the apparatus. Larsen's apparatus also includes a head cooling apparatus integrally connecting to the tubing of the main, body supported, apparatus for cooling the head of an individual. This once again is a cold surface cooling system that cannot compensate for the needs of the body. No layering of solid surfaces is addressed.

U.S. Pat. No. 5,289,695, issued to Parrish and Scaringe on Mar. 1, 1994 discloses a device for adsorbing water with a desiccant. Desiccants such as calcium chloride are mentioned. The exothermic heat generated by the hydration of this desiccant is blocked from the body by an open cell foam layer. Thinsulate by 3M could be used to help insulate along with the open cell foam. A molecular sieve is mentioned as well as an adsorbent or absorbent material. The desiccant can be sealed in a plastic bag which can be opened to initiate adsorption. Valves and pumping of fluids from the desiccant are mentioned. The use of a cold surface to reduce the humidity of the immediate environment is not mentioned.

U.S. Pat. No. 4,964,282, issued to Christopher S. Wagner on Oct. 23, 1990, discloses a detachable bulletproof vest air conditioning apparatus. Wagner's apparatus comprises a piping system that connects to a pre-cooled air source and ducts and channels the air into the interior of the vest, between the vest and the individual, to cool the wearer of said vest.

U.S. Pat. No. 5,146,625, issued to Sandra L. Steele and Harry W. Nettleton on Sep. 15, 1992, discloses a vest with cloth pockets that contain a phase shift material. No provision is made for the removal of moisture. No provision is made for providing channels to cool and dry air immediately below the phase shift material. No provision is made for the layering of said vest phase shift material. The phase shift material is enclosed in sealed bags that will proportionally thicken only relative to their width and thus reducing surface area to radiate heat and lengthen the freezing time required.

U.S. Pat. No. 5,072,455, issued to Thomas A. St. Ours on Dec. 17, 1991, discloses multiple pocketed vest with coolant packs. No provision is made for the removal of moisture. No provision is made for wicking the moisture to the cold packs nor is any provision made to channel the moisture out of the vest. The use of layering is not considered.

U.S. Pat. No. 4,170,793, issued to Scott T. O'Brien on Oct. 16, 1979, discloses a vest with a cotton inner lining which wicks moisture from the individual and allows for evaporation of moisture. No provision is made for actively absorbing the heat of the individual through a heat sink nor is there any provision for condensing the moisture of the individual so that it can be transported from the vest. No provision is made for layering or the flexibility of the vest.

U.S. Pat. No. 5,415,222, issued to David P. Colvin and Yvonne G. Bryant on Mar. 1, 1994, discloses a vest which has pouches of a coolant which does not cover the entire surface of the vest but rather allows evaporative cooling to occur where the pouches do not touch the wearer. No provision is made for the condensation and removal of moisture from the vest. Moisture is not condensed and channeled out in liquid form but rather is allowed to passively evaporate through pours in the vest. There are no channels for the transport of moisture or provision for the wicking of moisture to the channels. There is no provision for layering or for increasing the flexibility of the vest.

U.S. Pat. No. 6,125,645, issued to Stephen T. Horn on Oct. 3, 2000 teaches the removal of moisture by use of a cold surface. The patent was issued to the author of this patent application. What is not taught is the use of layers and its effects or the use of perforations in the heat sinks to both absorb moisture and transfer it to the environment. Nor is the effectiveness of two or more layers to extend the time of the vest or the time to re-freeze the vest. Nor is the effect of placing layers in a reverse shingled arrangement to provide dry air to the vest taught.

U.S. Pat. No. 6,915,641 B2 issued to Mark R. Harvie on Jul. 12, 2005 discloses a mechanical compressor system that cools the body. Harvie does not teach that sublimation within a gel packet and the gas released through a molecular sieve can cause cooling as is shown in the present invention.

Exothermal Tech makes a vest which has a phase change material designed to phase shift around 70 F in a sectioned plastic bag which is encased in a cloth shell. The sections are large and run diagonally no provision is made to wick moisture to these plastic bags. The close and immediate contact of the heat sink to the skin of the wearer prevents the removal of moisture from the body. The relatively high temperature of the phase shift material is insufficient to condense the moisture. There are no vertical channels in the sides of the vest to transport the condensed moisture. There is no provision for the use of layering to make the vest flexible or adjust the relative time the cooling effect will last.

3. SUMMARY OF THE INVENTION

The present invention allows the adjustment of a cooling vest to fit the particular necessities of a job. Often a person is required to go into a hot attic or other hot work environment to service some piece of equipment. Sometimes the job is only for a very short period such as to reset a motor circuit breaker or inspect insulation or other item. Sometimes the worker is forced to work in very cramped conditions that requires flexibility in a vest. In these cases a very light and flexible vest is needed while if the wearer needs to do further work then the vest needs to last longer. In these cases a vest with a substantial heat sink is used. These vests with a large thick and consequently heavy heat sink have a severe disadvantage. Their consequent thickness means that the time to refreeze them is greatly extended due to the fact that they can only radiate the absorbed heat only through their surface which is substantially smaller proportionally to a thin heat sink layer. This is so since the layers can be separated and laid out in a freezer where their heat can radiate faster. The inside layer is no longer encumbered from conducting the heat from it by surrounding warm material. It is believed that heat can be conducted and radiated from a number of thin heat sinks faster than a singular monolithic heat sink of the same weight. Thus a typical phase change material cooling vest can take a number of hours to refreeze and may require a special low temperature freezer to cool them in sufficient time.

The heat sink layers of the present invention by moving independent of each other make the vest more flexible. This is similar to the difference between trying to bend a board or bend a phone book. The phone book bends easily because the elements or pages slide relative to each other laterally and the board is a single element that maintains stiffness. The bulk and thickness of a monolithic heat sink in a cooling vest makes them stiff and inflexible when they are frozen because the inner portions of the heat sink do not move relative to each other. Sections may be essentially hinged to allow it to flex but again it is similar to hinged board sections. A hinge section generally flexes on one axis while a layered vest like a phone book can move on two axis. The inner portion of a monolithic gel section of a non layered cooling vest is also cold and it is believed therefore they tend to thicken and become less flexible relative to time and the force used. Water bends and conforms faster than ice. The heat sink in a typical cooling vest would then be comparable to a large block of ice. The present invention overcomes these objections by using a layered heat sink whose layers can slide almost water like, separately over each other and provide flexibility to the torso.

The layered heat sinks allow the wearer of a cooling vest also to adjust the length of time the vest will be effective according to the necessities of the particular activity. As for example a cooling vest can be worn with two layers of heat sinks to achieve active cooling for a particular length of time or can use three layers or more of heat sinks to lengthen the effective cooling time.

As a further advantage, the present invention uses a pair or more of heat sinks to create through free convection, it is believed, a very small amount of cold dried air which flows downward between the two cold plates or quilted frozen heat sinks. Warm moist air is drawn in at the top as heavy dense dry air exits the bottom of the heat sinks. Heat sinks in the present invention, may be arranged in a manner similar to a shingled roof with the slope reversed. Each layer being tucked under the next beneath it so that the cold heavy air is ducted to the body as it falls through the channels created by the quilted heat sink layers of vest.

The reader is asked to imagine a roof where the singles are reversed and when it rains all the water running down the roof is ducted into the house instead of to the next shingle. In the present invention the outside warm air is sucked through the channels between the layers from the flow of the heavier cold air downward and is deposited on the body of wearer after being cooled and somewhat de humidified. This process of air flow is seen commonly in a chimney that instead conducts hot air up ward. The effect of the conduction in the vest is to cool the body lower than the particular layer of the heat sink. It is believed this is done through both evaporation of body moisture and through conduction. The air is dried by condensing the moisture out of it and is condensed on the sides of the quilted heat sink channels. The air is also cooled by the transfer of heat to the heat sinks. Only a very small amount of air is needed to flow between the cold plates or layers of heat sink material to eliminate the feeling of clamminess on the body of the person. This small amount of dry air mixes with the surface air on the body and gives a sense of comfort. It is believed this sense of comfort is attributable to the body's ability to thermo regulate by the piloerection of small hairs next to the skin by the arrectores pilorum muscles and the emission of sweat and contraction of small capillary blood vessels just under the skin. The dry cool air allows the body to properly regulate its temperature. In normal circumstances the relative humidity under clothing and immediately next to the skin is quite high. At the point that the air next to the body adjusts below the dew point the body then can through evaporation cool further. The more layers that are used the greater the flow of dry cold air.

The present invention also uses small perforations approximately 0.002 inch in the plastic and Mylar coverings of the heat sink layers to absorb the condensed water in the channels formed between the layers or a layer and the body which limits blockage of the channels or excessive drainage of the water. The holes are believed to be resistant to liquid flow do to surface tension. It is believed the effect is overcome when substantial amounts of water build up in any portion of a channel; the liquid can be forced into the heat sink when the wearer moves in a manner placing the liquid under pressure over the perforation in the covering of the heat sink material and over coming the surface tension. The water there mixes with a thickening agent solution, as is common in baby diapers, in the quilted pocket with the thin layer of liquid surrounding the frozen center of the quilted pocket. The water, thus introduced to the inside of the heat sink, can in turn be passed through similar perforations on the outer side of the quilted heat sink layer as a vapor over time or especially when the environment is extremely hot and dry as it typically is in attics in arid hot locations. This sublimation of the liquid in the heat sink to a gas and the subsequent release of this gas, cools the vest. But the water in the vest does not leak out it is believed because of it mixing or mechanically or chemically bonding with the thickening agent. Sodium polyacrylate is a good choice of thickening agents because it can absorb hundreds of times its weight in water. This polymer type material tangles with others and forms lumps which become resistant due to their size to passing through the penetrations; it is believed. The water can penetrate the surface of the heat sink dependent on the phase it is in and the pressure it is exposed to. Surface tension and the bonding of the thickening agents are believed to be factors in this transfer of water across the surface of the heat sink. Different circumstances occur at different times and on different places on the heat sink. One should envision an ice cube of sorts but one that is not pure water but bound with a thickening agent. The ice cube is supported in a bag and the bag has very small holes in it. The ice cube necessarily has a thin layer of liquid around it that is bound to a thickening agent. Water lock that is used in baby diapers is an excellent agent as has been stated. The holes allow liquid water to pass into the bag through the small perforations when the surface tension is broken and the water lock or polymer type gel material is not completely saturated. The hole also allows the passage of water in its gas or vapor form. The holes under greater pressure will allow the passage of the liquid as when the bag is severely squeezed such as when the vest is forced to conform against the body as when bending. The water, it is believed being stripped from the polymer and the polymers being broken by the force. Thus liquid water can be introduced and transferred through the heat sink and evaporated out the other side while adding to the sliding qualities of the layers under greater force as a lubricant. The phase shift of the water to a gas in the vest can be used to reduce the weight of the vest or increase the duration of the vest and provide comfort to the wearer.

Temperatures of 160 F. and humidity of 20% are thought to be common in attics in Texas and Nevada. The pressures to force the water into the heat sink through the perforations can be between two quilted layers of heat sink or between the body and the heat sink. The insulating layer often between the body and the heat sink but not always is water permeable. Experiments by the inventor using air pressure to measure the amount of pressure found under cooling vest heat sinks shows that pressures of 30 psi in localized areas are not uncommon.

The present invention thus cools the body by a number of ways other than just conduction. The vest does cool by conduction but also cools by condensing the moisture out of the thin layer of air immediate to the body and thus allows evaporative cooling of the skin. The subsequent condensed moisture can be forced with movement of the body through small holes in the heat sink casing. The heat sink absorbs heat from the air surrounding the body by conduction and the subsequent phase shift of the heat sink material. The heat sink material as it shifts to a liquid is surrounded by the liquid and on the outside of the heat sink where it is exposed to environmental heat the liquid again phase shifts to a gas and passes through the holes in the heat sink covering. A molecular sieve could be used as well and possible more effectively. A layer similar to the product brand Gortex will allow vapor to pass but not liquid water. Due to the nature of the particular constructions of these materials more water in a liquid state could be phase shifted to a gas and more cooling efficiency could be achieved.

An insulating layer protects the person from the uncomfortable conduction of heat directly to the heat sinks. The insulating layer should allow the transfer of moisture to the heat sinks and allow the displacement of humid air next to the skin with cooler air. An excellent heat sink is frozen water because of the large energy absorption necessary to phase shift ice into a liquid and its safety.

Further objects and advantages of my invention will become apparent from a consideration of the drawings and or ensuing description.

4. BRIEF DESCRIPTION OF THE DRAWINGS

FIG. 1 is a perspective drawing of a person with cooling vest on and kneeling. FIG. 1 number 1 shows a doted line indicating the body surface of the person acting as a supporting structure that is forcing the heat sink layers, FIG. 1 number 2, to bend and slide against each other and shift lateral location. This is a lateral shift that allows the bend to occur with less force being applied and over a tighter radius than would be possible with a monolithic heat sink equaling the thickness of the two layers combined. FIG. 1 number 2, also shows a pressurized area between the two shown heat sink layers which is caused by the squeezing or pinching action of the bending of the persons body. Under this force the contents of the inner layer heat sinks would be expressed through the small holes or penetrations in the surface of the heat sink and lubricate the sliding heat sink layers. Forces larger than the force to break surface tension are believed necessary to pressurize contents from the interior of a heat sink to the exterior. Moisture or contents of the heat sink are re absorbed it is believed upon the release of the pressure much like a sponge.

FIG. 2 shows the layers sliding in detail. FIG. 2 number 3 shows a heat sink quilted section viewed on end. FIG. 2 number 1 shows a supporting structure bending the normally parallel layers into sliding laterally against each other, FIG. 2 number 5.

FIG. 3 shows a quilted heat sink laying on a supporting structure. FIG. 3 number 3 shows a quilted heat sink attached to the supporting vest and FIG. 3 number 6 shows the outside of the vest, FIG. 3 number 7 shows inside of the vest.

FIG. 4 is a drawing of just the quilted heat sink in end view. FIG. 4 number 8 shows a channel that allows the flow of air both between layers an and between the heat sink and a supporting surface number 1.

FIG. 5 is a drawing of the quilted heat sink when folded or bent by a supporting structure. FIG. 5 number 9 is an area where the pressure it is believed to be at times higher than surface tension and consequently can force moisture condensed from the supporting structure, FIG. 5 number 1, into the quilted heat sink when the quilted heat sink is not saturated or is under saturated nor is it frozen solid.

FIG. 6 is a drawing of the quilted heat sink flat or front view. The quilted Mylar packets are visible as well as the channels FIG. 6 number 8, between individual heat sink cells FIG. 6 number 10. FIG. 6 number 11 shows the area where penetrations are or a molecular sieve is.

FIG. 7 shows right lateral side end on of the quilted heat sink layer. FIG. 7 number 8 shows the channel that allows the flow of air below the velcro. Number 12 FIG. 7 shows the velcro loop side and number 13 FIG. 7 shows the velcro hook side FIG. 8 shows, number 12 the velcro loop, the hook is on the opposing side and not shown. Number 14 FIG. 8 shows the outer flat surface edge of the quilted heat sink layer. Number 15 FIG. 8 shows the raised quilted part of the heat sink layer.

Figure 9:
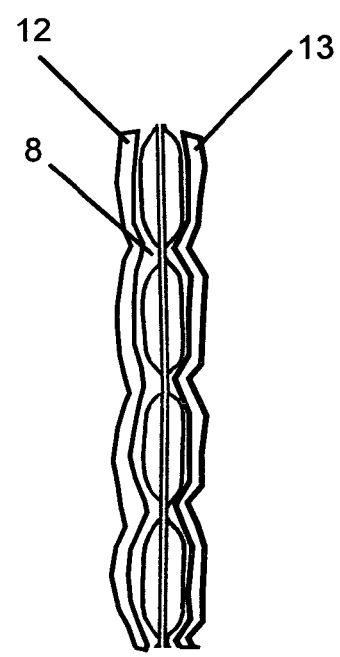

FIG. 9 shows the top view showing the irregular fit of the velcro as it is attached to the heat sink layer. It conforms somewhat to the raised quilted heat sink but not completely. FIG. 9 number 8 shows the air channel under the velcro loop number 12. FIG. 9 number 13 shows the velcro hook on the opposing side.

5. DETAILED DESCRIPTION OF THE PREFERRED EMBODIMENT(s)

The preferred vest would be a fabric shell with a large zipper that would encompass the entire front of the vest and another zipper that would encompass the back of the vest. The inner layer of the vest would be a permeable hydrophobic layer that would insulate the heat sinks from contact with the skin. The heat sinks would be a mylar or similar plastic laminated in a quilted fashion to provide channels for air flow. The channels would be closer than three linear inches apart. The laminated heat sinks would hold water or a eutectic gel or a water and chemical such as used in disposable baby diapers. These heat sinks would Velcro in with Velcro on both sides of the top of the heat sinks so that more than one quilted heat sink layer could be attached to the vest shell. Although other methods could be used. The vest would have at least two bands of quilted heat sink surrounding the torso of a person. The bands could hold a number of layers. Each successive band could tuck into the layer beneath it to deliver dry air the to the permeable insulating layer next to the skin. The heat sink layers would be reflective to infrared on the outside and away from the body. A thin layer of cloth would cover the reflective layer to reduce heat absorption from the environment through conduction.

Specific to the heat sink, small holes would perforate the heat sink of such a diameter that surface tension would prevent leakage of liquid but allow vapor to evaporate under heat stress from the environment and thus lengthen the cooling time of the vest relative to the weight. Thus a frozen solid gel contained within a section of the heat sink would sublimate on its exterior surface to a liquid. The liquid would be retained within the heat sink by a molecular sieve and or the water absorbent and sponge like gel. As the liquid again sublimated into a gas it could pass through either small holes or through a molecular sieve and cool the vest further. These small perforations under pressure on the inside of the vest would allow condensed water to be squeezed back into the vest to rehydrate the quilted heat sinks when the wearer moved and over came the inherent surface tension. The water mixes with the thickening agent and can only leave primarily as a vapor or gas. The size of the holes could be made more tolerant to overt leakage by the use of a gel or thickening agent rather than just water.

It is intended that further embodiments incorporating the spirit of the invention to one skilled in the art, fall within the scope of this invention.

A channel is any space through which air can flow. It can be thin and broad or created by the quilting of the material in the heat sink. A channel may be created by placing two objects in close proximity or covering it with a third object thus creating a passage through which air can flow.

A heat sink is anything that is colder than the surrounding environment. In a cooling vest it can be cold plates or inserts that are attached to a vest of any material that will effectively absorb heat such as frozen water or eutectic gel in a quilted Mylar package.

Heat absorption is the flow of heat from a hot body to a cold body.

A perforation is a hole that will allow something to pass through it.

A eutectic gel is a compound found in cooling vests that absorbs heat through a phase shift. It can include sodium polyacrylate.

To Velcro something in is to use a hook and loop fastener to attach something to the vest although it can also mean to attach by other similar means such as snaps or even double sided tape.

Something is quilted when it has sunken seams between areas or channels of reduced thickness of the material.

Permeable means something can flow through it like water and cloth.

A molecular sieve is a material that will allow one phase of a material to pass but restrict the passage of the same material in a different phase. Small perforations can with some materials do this.

A thickening agent is a material that locks with the water in a manner of the common material in baby diapers. It absorbs the water in its liquid state and unlike a sponge does not readily release the water when under light pressure. Sodium polyacrylate is a thickening agent.

Moisture saturation point is the point where the water cannot be readily evaporated into the air because the humidity is to high for the temperature.

Heat sink layers are layers of heat absorbing material laid normal to the body where the layers are sandwich like with one on the top of another.

A supporting means is a supporting structure something that can give support to something. It can be stiff or soft. I can be a human body or a human body covered in cloth or it can be something that could not support the object itself unless it was also supported. It can be a surface to which force can be applied.

Something is saturated when it can not absorb anything anymore.

Sublimation is the change from a solid to a liquid or a gas or liquid to a gas.

I claim:

1. A cooling garment comprising:
    two or more heat sinks in a layered configuration, each heat sink attached to the cooling garment such that non-affixed portions of the heat sinks are able to move independently of each other.

2. The cooling garment of claim 1, wherein each heat sink is attached to the cooling garment along a top of the heat sink.

3. The cooling garment of claim 1, further comprising:
    attachment means for attaching the two or more heat sinks to the garment.

4. The cooling garment of claim 3, wherein the attachment means comprises hook and loop fasteners.

5. The cooling garment of claim 1, further comprising:
    a hydrophobic spacer attached to the cooling garment such that the hydrophobic spacer is between a body of a wearer of the garment and an innermost one of the two or more heat sinks.

6. The cooling garment of claim 1, wherein at least one of the two or more heat sinks comprises a quilted structure, thereby forming a plurality of substantially vertical channels.

7. The cooling garment of claim 1, wherein at least one of the two or more heat sinks comprises a frozen heat sink.

8. The cooling garment of claim 1, wherein at least one of the two or more heat sinks comprises a plurality of perforations in an outer covering of at least one heat sink to enable water that has condensed on the outer covering to enter at least one heat sink.

9. The cooling garment of claim 1, wherein each heat sink is attached to the cooling garment such that the non-affixed portions of the heat sinks are able to slidably move independently of each other.

10. The cooling garment of claim 1 wherein at least one of the two or more heat sinks comprises a plurality of penetrations in an outer surface of at least one heat sink where it is adjacent to another said heat sink to enable the contents of first said heat sink to be expressed under pressure and thus lubricate the adjacent surfaces between first and second said heat sinks.

11. A method of cooling comprising:
    providing a cooling garment, the cooling garment comprising:
        two or more heat sinks in a layered configuration, each heat sink attached to the cooling garment such that non-affixed portions of the heat sinks are able to move independently of each other.

12. The method of claim 11, wherein each heat sink is attached to the cooling garment along a top of the heat sink.

13. The method of claim 11, wherein the cooling garment further comprises:
    attachment means for attaching the two or more heat sinks to the garment.

14. The method of claim 13, wherein the attachment means comprises hook and loop fasteners.

15. The method of claim 11, wherein the cooling garment further comprises:
    a hydrophobic spacer attached to the cooling garment such that the hydrophobic spacer is between a body of a wearer of the garment and an innermost one of the two or more heat sinks.

16. The method of claim 11, wherein at least one of the two or more heat sinks comprises a quilted structure, thereby forming a plurality of substantially vertical channels.

17. The method of claim 11, wherein at least one of the two or more heat sinks comprises a frozen heat sink.

18. The method of claim 11, wherein at least one of the two or more heat sinks comprises a plurality of perforations in an outer covering of the at least one heat sink to enable water that has condensed on the outer covering to enter the at least one heat sink.

19. The method of claim 11, wherein at least one of the two or more heat sinks comprises a plurality of penetrations in an outer surface of at least one heat sink where it is adjacent to another said heat sink to enable the contents of first said heat sink to be expressed under pressure and thus lubricate the adjacent surfaces between first and second said heat sinks.

20. The method of claim 11, wherein each heat sink is attached to the cooling garment such that the non-affixed portions of the heat sinks are able to slidably move independently of each other.

\* \* \* \* \*